United States Patent [19]
Orth

[11] Patent Number: 5,445,613
[45] Date of Patent: Aug. 29, 1995

[54] CONDITION DETECTION SYSTEM AND CLAMP

[75] Inventor: Jeffrey L. Orth, Salt Lake City, Utah

[73] Assignee: Rocky Mountain Research, Inc., Salt Lake City, Utah

[21] Appl. No.: 93,369

[22] Filed: Jul. 16, 1993

[51] Int. Cl.⁶ ............... A61M 31/00; A61M 5/00; F16K 7/04; F16K 31/00
[52] U.S. Cl. .................... 604/66; 604/67; 604/250; 251/5; 251/14
[58] Field of Search .......... 604/30, 31, 34, 65–67, 604/246, 250; 251/5, 14

[56] References Cited

U.S. PATENT DOCUMENTS

| | | | |
|---|---|---|---|
| 4,327,724 | 5/1982 | Birk et al. | 604/119 X |
| 4,345,594 | 8/1982 | Bisera et al. | 604/67 X |
| 4,421,506 | 12/1983 | Danby et al. | 604/34 |
| 4,482,345 | 11/1984 | Chow et al. | 604/31 |
| 4,714,463 | 12/1987 | Archibald et al. | 604/81 |
| 4,782,817 | 11/1988 | Singh et al. | 600/17 |
| 4,899,783 | 2/1990 | Yusko et al. | 137/556 |
| 4,925,152 | 5/1990 | Hüber | 251/5 |
| 5,154,704 | 10/1992 | Archibald | 604/250 |
| 5,242,404 | 9/1993 | Conley et al. | 604/119 |
| 5,244,463 | 9/1993 | Cordner, Jr. et al. | 604/131 |

FOREIGN PATENT DOCUMENTS 9007353  7/1990  WIPO ................ 604/250

OTHER PUBLICATIONS

*The Oxford English Dictionary*, 2nd ed., vol. IX (Clarendon Press, 1989), p. 535.
*Mark's Standard Handbook for Mechanical Engineers*, 9th ed. (McGraw-Hill, 1987), pp. 15–75 to 15–78.
*Electronics Engineers' Handbook*, 3rd ed. (McGraw-Hill 1989), pp. 10–2 to 10–12.

Primary Examiner—John D. Yasko
Assistant Examiner—Adam J. Cermak
Attorney, Agent, or Firm—Trask, Britt & Rossa

[57] ABSTRACT

A clamping device for obstructing the flow of fluid through a tube is disclosed which may be electrically or manually actuated in response to an electrical signal from a condition detection means associated with the tube. The clamping device may also be actuated to compress the tube gradually, providing incrementally decreasing flow through the tube.

31 Claims, 7 Drawing Sheets

CONDITION DETECTION SYSTEM AND CLAMP

BACKGROUND

1. Field

This invention relates generally to clamping devices for compressing a tube to obstruct the flow of fluid therethrough. Specifically, this invention relates to clamping devices associated with medical apparatus for closing off tubes through which a fluid, such as blood, may flow, and more specifically to clamping devices which close in response to the detection of a condition in the fluid flowing through the tube.

2. State of the Art

Devices for temporarily clamping resilient tubes to temporarily prevent a fluid from flowing through the tube are well-known. Such clamping devices are often used in association with medical equipment, and are frequently used in connection with medical apparatus which perform circulation of fluids to or from a living body. An example of such a device is disclosed in U.S. Pat. No. 5,062,775 for an extracorporeal support system which operates to circulate blood from a patient through the device and to return the blood to the patient.

Clamping devices take various forms, but typically function by the manually or electrically induced engagement of structure which pinches the tube at a particular location to prevent passage of fluid through the tube. Some clamping devices are connected to means for detecting a specific condition in the fluid which, when the condition occurs, triggers the clamping or unclamping of the tube. For example, it may be desirable to terminate blood flow through a tube if the hematocrit level falls above or below a certain value. For example, if the hematocrit level drops, as sensed by a detection means, an electrical signal is relayed to the clamping device causing it to close off the tube.

Clamping devices currently in use are capable of generally accommodating only those tubes which have a small internal diameter (approximately 1 millimeter to 5 millimeters) and which are very pliant. Further, clamping devices currently in use maintain either a fully opened or a fully closed condition. That is, the tube positioned within the clamp may be either completely uncompressed (open tube) or completely compressed, but may not be partially compressed. Such clamping devices cannot provide incrementally increasing compression of the tube as may be required by some medical procedures. In addition, many clamping devices do not provide means for manually operating the clamping device under emergency situations, such as a power failure, or as may be dictated by medical necessity.

Thus, there remains a need for a clamping device which can accommodate both smaller internal diameter tubes as well as larger internal diameter tubes which are relatively less flexible. There also remains a need for a clamping device which provides for gradual compression of a tube, and which can be manually operated to compress the tube to varying degrees.

SUMMARY OF THE INVENTION

According to the present invention, a clamping device is provided which may be operated in both powered and manual modes, and which provides optional incrementally increasing compression of the tube to which it is attached. The clamping device of the present invention is structured to provide compression of larger diameter tubes and tubes which are relatively less pliant due to a greater tube wall thickness or some other structural chacteristic. While the present invention is suitable for many conditions in which flow of a fluid in a tube is desirably terminated by use of a clamping device, the use of the present invention in medical applications is described below by way of example.

The present invention is structured to accommodate tubes having relatively larger internal diameters; e.g., thirty millimeters or more. Because larger tubes tend to be constructed of materials which are less pliant or flexible than smaller tubes, the present invention is structured to adequately compress such larger tubes to assure complete obstruction of the tube. The clamping means generally includes a clamping structure associated with movable compression means, such as a plunger or piston. The plunger causes the clamping structure, which may include a clamping bar, to converge with a base on which the tube rests. As the clamping bar approaches the base, the tube becomes compressed therebetween. The clamping device may also include support means for maintaining the tube between the clamping bar and the base. The present invention can also accommodate tubes of smaller size constructed of more flexible material.

The present invention provides compression of a tube by actuation of power means associated with the compression means or by manual depression of the compression means. The power means may include a solenoid or other appropriate apparatus, such as pneumatic or hydraulic means, for providing force to the compression means. A spring mechanism may be associated with the compression means to provide reciprocal force to the compression structure mechanism to thereby open the tube again. Conversely, the spring mechanism may provide the compression force and the power means may provide the reciprocal, opening force.

The present invention may be connected to means for detecting a particular condition in the fluid or in the flow which may be employed for trigger actuation of the clamping device. Many such means exist in the art and may be used with the present invention. By way of example, however, such means for detecting an extant condition are described herein with respect to air detection devices. A typical air detection device may comprise a transducer which is associated with the tube. A transducer is generally capable of detecting the presence of air within a fluid, and sends an electrical signal to the power means of the clamping device to actuate it. In certain medical applications, the known directional flow of fluid in the tube may be critical to the therapy or procedure, and flow detectors may also be associated with the clamping device to prevent back flow of fluid through the tube.

The present invention also includes indication means for indicating to the user that the clamping structure is properly engaged to fully compress the tube, and for indicating when adequate clamping has not occurred.

DESCRIPTION OF THE ILLUSTRATED EMBODIMENTS

Figure 1:
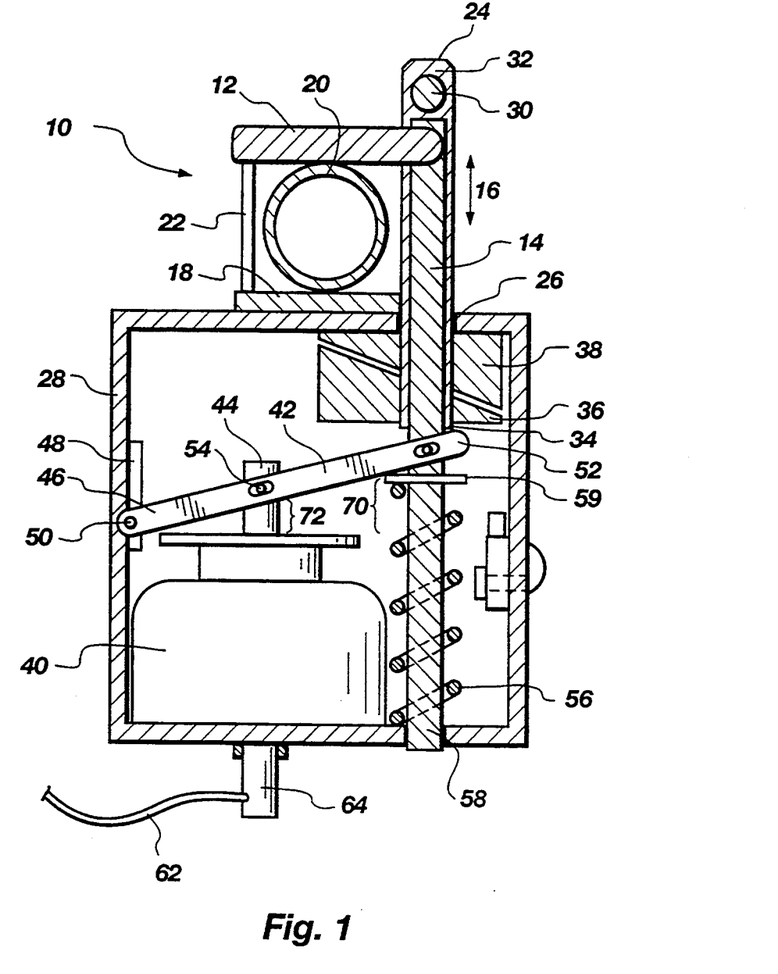
FIG. 1 is a side view in cross-section of a clamping device of the invention showing it in the open position.
Figure 2:
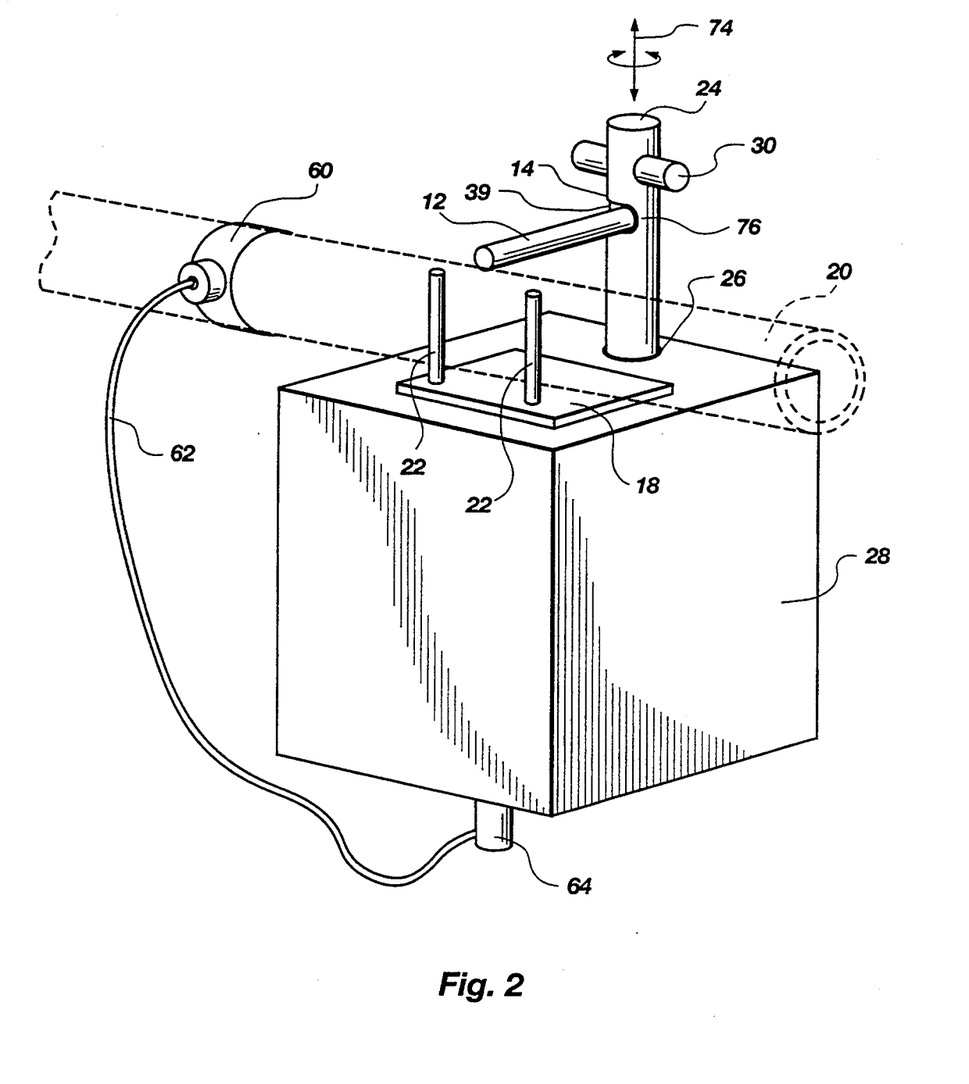
FIG. 2 is a perspective view of the clamping device shown in FIG. 1 with some parts shown in phantom line.

As illustrated by FIG. 1, the clamping structure, generally at 10, comprises a clamping bar 12 connected to a movable plunger 14. The plunger 14 is capable of moving up and down, as indicated by arrow 16, and thus clamping bar 12 is movable in the same directions. When the plunger 14 moves downwardly, the clamping bar 12 approaches base 18, and compresses the tube 20 which is positioned between the clamping bar 12 and the base 18. Support means 22 assist in maintaining the tube 20 in position between the clamping bar 12 and the base 18. FIG. 2 more clearly illustrates the placement of the tube 20 between the clamping bar 12, the base 18 and the support means 22 which keep the tube 20 positioned therebetween.

Plunger 14 is slidably disposed within a sleeve 24 which is itself slidably positioned within an aperture 26 formed in a housing 28 containing the other structures of the device. A handle 30 is provided proximate the upper end 32 of the sleeve 24 to facilitate manual rotation of the sleeve 24, as described further below. The lower end 34 of the sleeve 24 is secured to a movable cam 36 which is biased against a stationary cam 38. As illustrated by FIG. 2, the clamping bar 12 extends outwardly from the plunger 14 through a slot 39 formed in the sleeve 24.

Solenoid 40 is positioned within housing 28 and has a lever arm 42 attached to its core 44. Solenoid 40 may be powered by any suitable electrical source (not shown). The lever arm 42 has a first end 46 connected to a retainer plate 48 via pivot pin 50 in a manner which allows the first end 46 of the lever arm 42 to pivot about a generally horizontal pivot pin 50. The retainer plate 48 is secured to the housing 28. A second end 52 of the lever arm 42 is connected to the plunger 14 in a manner which allows the lever arm 42 to articulate with the plunger 14 as the plunger 14 moves up and down. The lever arm 42 is attached, at about its mid-section 54, to the core 44 of the solenoid 40, and is attached in a manner which allows the lever arm 42 to articulate with the core 44 as the lever arm 42 and core 44 move up and down. A spring mechanism 56 is associated with the lower end 58 of the plunger 14, and is biased against a ring 59.

The present invention is particularly suitable for use with medical equipment, and is particularly directed to extracorporeal treatment of blood. Extracorporeal blood systems generally comprise tubing which carries arterial blood away from the patient and into blood treatment apparatus. The tubing is typically connected to a pump which assists in circulating the blood from the patient through the tubing for treatment. The blood may be treated by any means such as dialysis, filtration, oxygenation or the like. The blood is then returned to the patient through tubing which delivers the blood into the venous system of the patient.

Before blood is returned to a patient, it may be necessary or desirable to assure that a particular condition exists with respect to the blood. For example, it is important to be assured that no air bubbles have been introduced into the blood before it is returned to the body. Therefore, air detection means are connected to the arterial tubing. As illustrated by FIG. 2, condition detection means 60 may be positioned on the tubing 20 upstream from the clamping device. Electrical communication means 62 interconnects the condition detection means 60 to the lower end 64 of the coil of the core 44 of the solenoid 40. The term "core," as used herein, describes the combined plunger and encircling coil of a conventional solenoid. The condition detection means 60 may be any type of device which can detect the particular condition within the tube and which can signal the clamping device to compress the tube, as described further below. The condition detection means 60 may, for example, be air detection means. Transducers are particularly suitable for this application, and may themselves be of several different types. An ultrasound transducer is particularly suitable, however, as an air detector.

Figure 3:
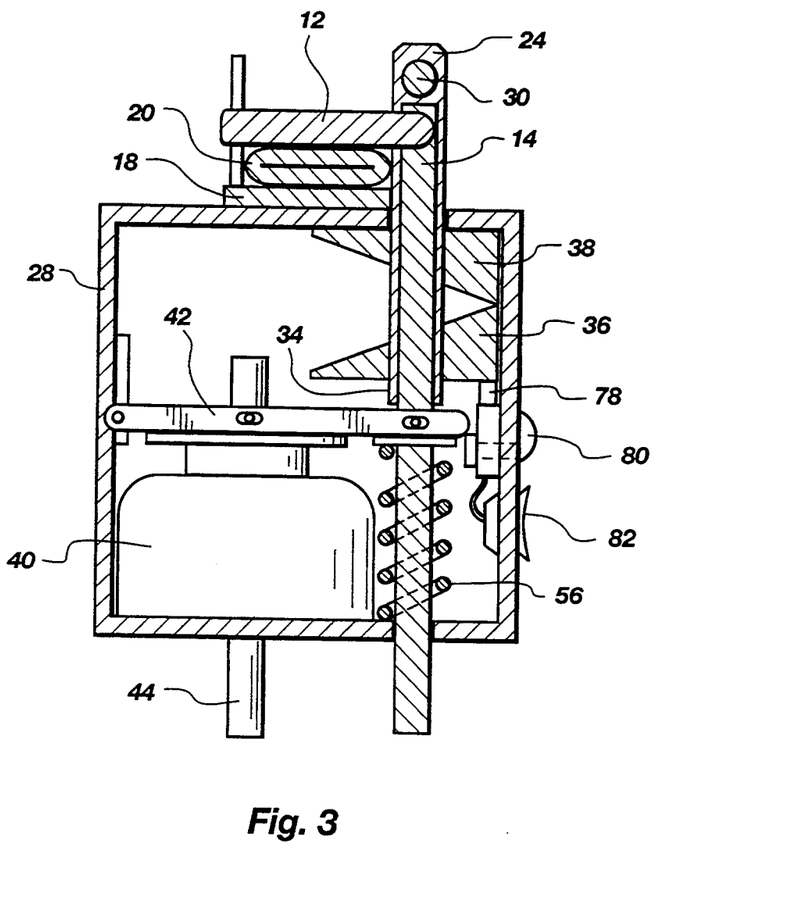
FIG. 3 is a side view in cross-section of the clamping device shown in FIG. 1 illustrating it in the closed position compressing the tube.

In operation, when the air detection means (e.g., 60) or transducer detects air in the tube, an electrical signal is sent via the electrical communication means or wire 62 to the coil of the core 44 of the solenoid 40 thereby actuating it. As illustrated by FIG. 3, the plunger of the core 44 is urged downwardly, and as it moves, the lever arm 42 moves downwardly also. As plunger 14 moves downwardly, it urges the clamping bar 12 to move downwardly also. Downward movement of the clamping bar 12 causes the sleeve 24 to move downwardly, which urges the movable cam 36 to move downwardly. The clamping bar 12 thereby approaches the base 18 and compresses the tube 20 between the clamping bar 12 and the base 18. The spring mechanism 58 is compressed between the bottom of the housing 28 and the ring 59.

As long as the electrical signal from the transducer (e.g., 60) is communicated to the solenoid 40, the clamping bar 12 continues to compress the tube 20. Once the signal has terminated, the plunger of the core 44 of the solenoid 40 is no longer drawn downwardly by electromagnetic force and the spring mechanism 58 urges the ring 59 upwardly, thereby causing the lever arm 42 to move upwardly. Movement of the plunger 14 upwardly causes the clamping bar 12 to move upwardly terminating compression of the tube 20. It can be seen by FIG. 1 that advantage is gained by the configuration of the present invention by the ratio of the force provided by the solenoid to the force applied on the clamping bar, as illustrated by the distance 70 traveled by the second end 52 of the lever arm 42 which is markedly longer than the distance 72 the core 44 moves. The stroke distance advantage gained is particularly valuable since a smaller displacement solenoid 40 may be used to ultimately achieve compression of a larger diameter tube 20 than may otherwise be possible.

The tube 20 may also be compressed by manual actuation of the lever arm 42. As illustrated in FIG. 2, clamping bar 12 projects outwardly from the plunger 14 through a slot 39 formed in the sleeve 24. The slot 39 is formed horizontally through the wall of the sleeve 24 and is sized in length to allow a 180° rotation of the sleeve 24 about a vertical axis 74. When the plunger 14 is fully extending upwardly so that the clamping bar 12 is not compressing the tube 20, the clamping bar 12 rests against one end 76 of the slot 39. When the sleeve 24 is rotated 180°, the clamping bar 12 rests against the opposite end (not shown) of the slot 39.

Figure 4:
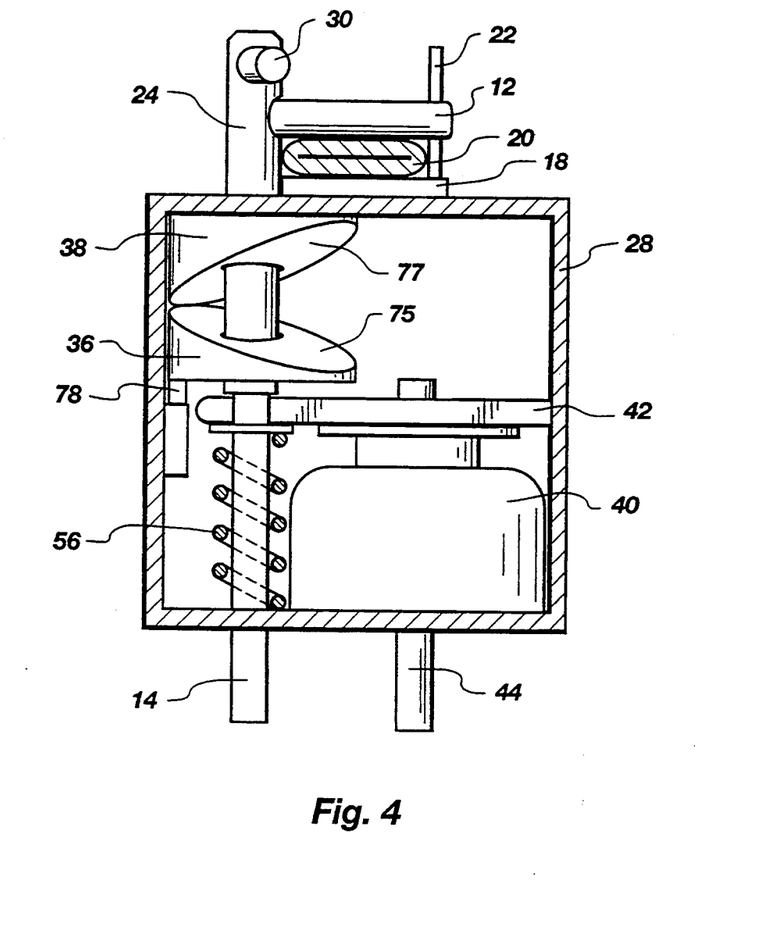
FIG. 4 is a cross-section view of the clamping device, shown from the side opposite the side shown in FIGS. 1 and 3.

As illustrated by FIG. 3, when the handle 30, or manual actuation means, is rotated, thereby causing sleeve 24 to rotate, the movable cam 36 to which the bottom 34 of sleeve 24 is attached is caused to rotate. Movable cam 36 has a flat, sloped, and slightly tilted face 75, as illustrated in FIG. 4, which biases against a corresponding flat, sloped and slightly tilted face 77, as illustrated in FIG. 4, of stationary cam 38. Movable cam 36, biased against stationary cam 38, is drawn downwardly thereby urging sleeve 24 and plunger 14 downwardly. Clamping bar 12 again approaches base 18 and compresses the tube 20 therebetween. When the handle 30 is released, the spring mechanism 56 urges the plunger 14 and sleeve 24 upwardly thereby causing the sloped face 75 of the movable cam 36 to rotate against the sloped face 77 of the stationary cam 38 until the sloped faces 75 and 77 are positioned adjacently facing each other again, and sleeve 24 and plunger 14 are fully extended, as shown in FIG. 4.

The ability to manually actuate the clamping device to compress the tube 20 is particularly advantageous to certain medical procedures. For example, when blood is being circulated through an extracorporeal treatment device during cardiopulmonary bypass, the patient must ultimately be weaned from the extracorporeal device to allow the body to function independently again. It is valuable, therefore, to be able to gradually compress the tube 20 with the clamping bar 12, gradually reducing the flow of blood from the body until the patient is weaned from the extracorporeal device.

When the plunger 14 is urged downwardly, the movable cam 36 contacts a switch 78 which causes an indicator light 80 positioned on the outside of the housing 28 to become lit. Thus, when the clamping bar 12 fully approaches the base 18 and compresses the tube 20 completely, the indicator light 80 will so indicate. Electrical circuitry interconnecting the air detection means (e.g., 60) and the solenoid 40 also interconnects with switch 78 and alarm 82. The electrical circuitry is structured to receive feedback from the switch 78. If the air detection means (e.g., 60) detects air in the tube 20 and signals the clamping bar 12 to compress the tube 20, feedback from the switch 78 normally signals the circuitry that the switch 78 has been contacted by the movable cam 36 verifying that the tube 20 is fully compressed. However, if no feedback is received from the switch 78 the alarm 82 will be energized, emitting an audible sound of alarm. Circuitry to effect the foregoing results is well-known in the art and, therefore, will not be described further herein.

In certain applications, it may be desirable or necessary to have fluid in the tube 20 monitored; that is, it may be necessary to have flow in only one direction. If, for example, the centrifugal pump of an extracorporeal device should fail, the blood would be able to flow backwards from the arterial tubing to the venous tubing. In such eventualities, the condition detection means 60 may take the form of a flow direction monitor. A flow direction monitor which is especially suitable for this application makes use of Doppler ultrasound. Transit time ultrasound detection means using single or dual pairs of piezo crystals may also be used. A flow direction monitor may be linked with the tube 20 at the same time an air detection means is linked to the tube, and may be configured in any appropriate manner to properly trigger compression of the clamp.

Many medical procedures require apparatus which have clamping means linked to the arterial and/or venous tubes. Therefore, the present invention is intended for use in such procedures, and provides for the integration of two or more clamping devices to a single condition detection means. For example, in the case of an extracorporeal support system, an air detector transducer connected to the arterial tubing (returning to the body) may be in electrical communication with a clamping device downstream from the transducer and with a clamping device positioned proximate the venous tubing. Thus, if air is detected in the tube, a signal is sent to both clamping devices causing them to obstruct the tubing to prevent flow of blood from the patient into the extracorporeal system, and to prevent any blood from returning to the patient. Alternatively, a third clamping device may be located on the tubing connecting the venous and arterial lines and operating in a closed-tube mode by constant actuation of the solenoid which is thereafter caused to become uncompressed to open the tube in response to a signal from a detection device.

The clamping device, detection means, and applicable logic circuitry may be configured in any manner to provide optimal clamping of the tube. For example, it may be desirable to impose a delay between the signal to close the venous line and the signal to close the arterial line in order to prevent outgassing of arterial blood which has not been fully circulated through the pump and the oxygenator. Delays, when necessary, may be imposed by modifications to the solenoid or whatever other power means are used to actuate the clamping bar.

Figure 5:
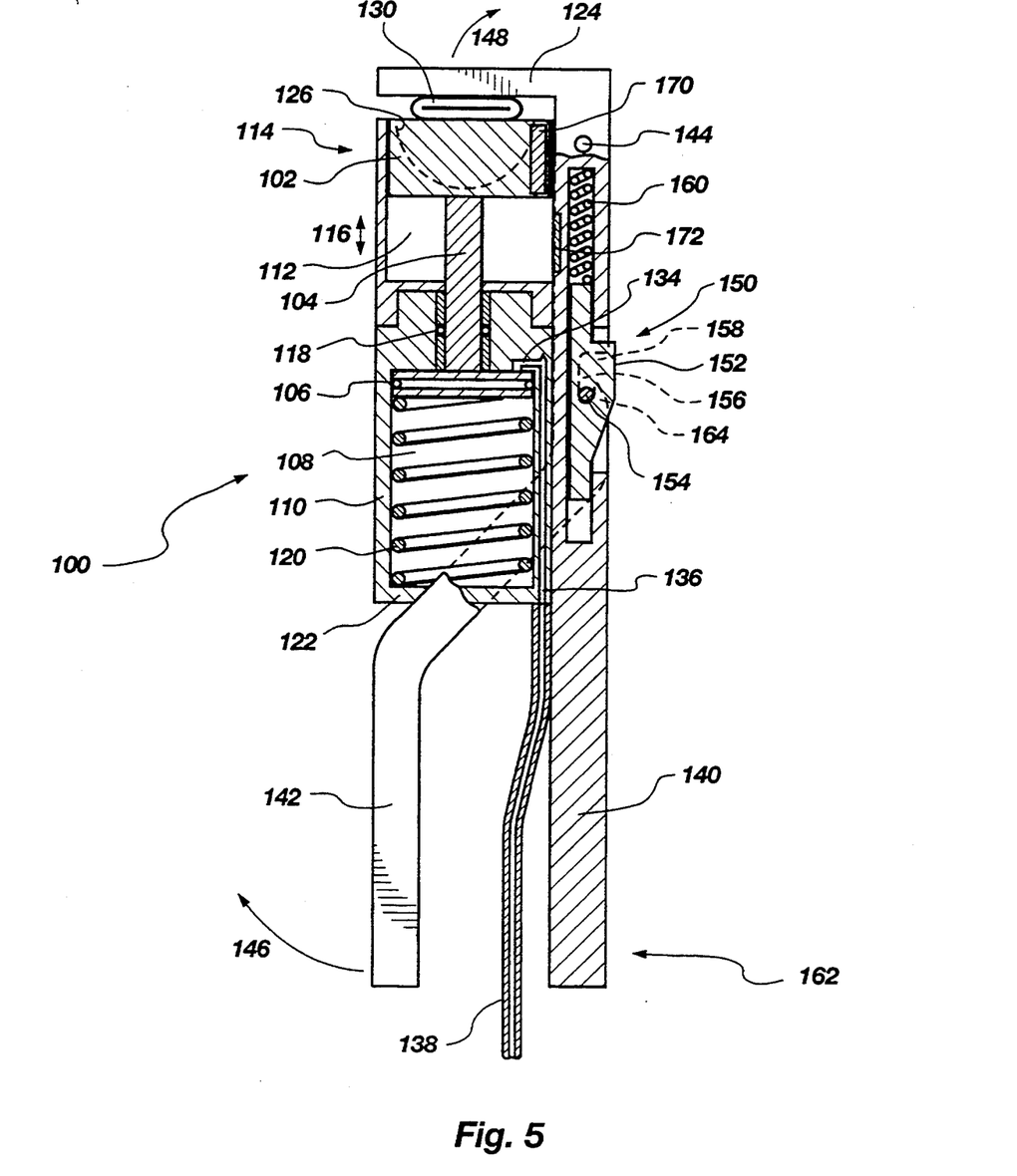
FIG. 5 is a side view in cross-section of an alternative embodiment of the invention.
Figure 6:
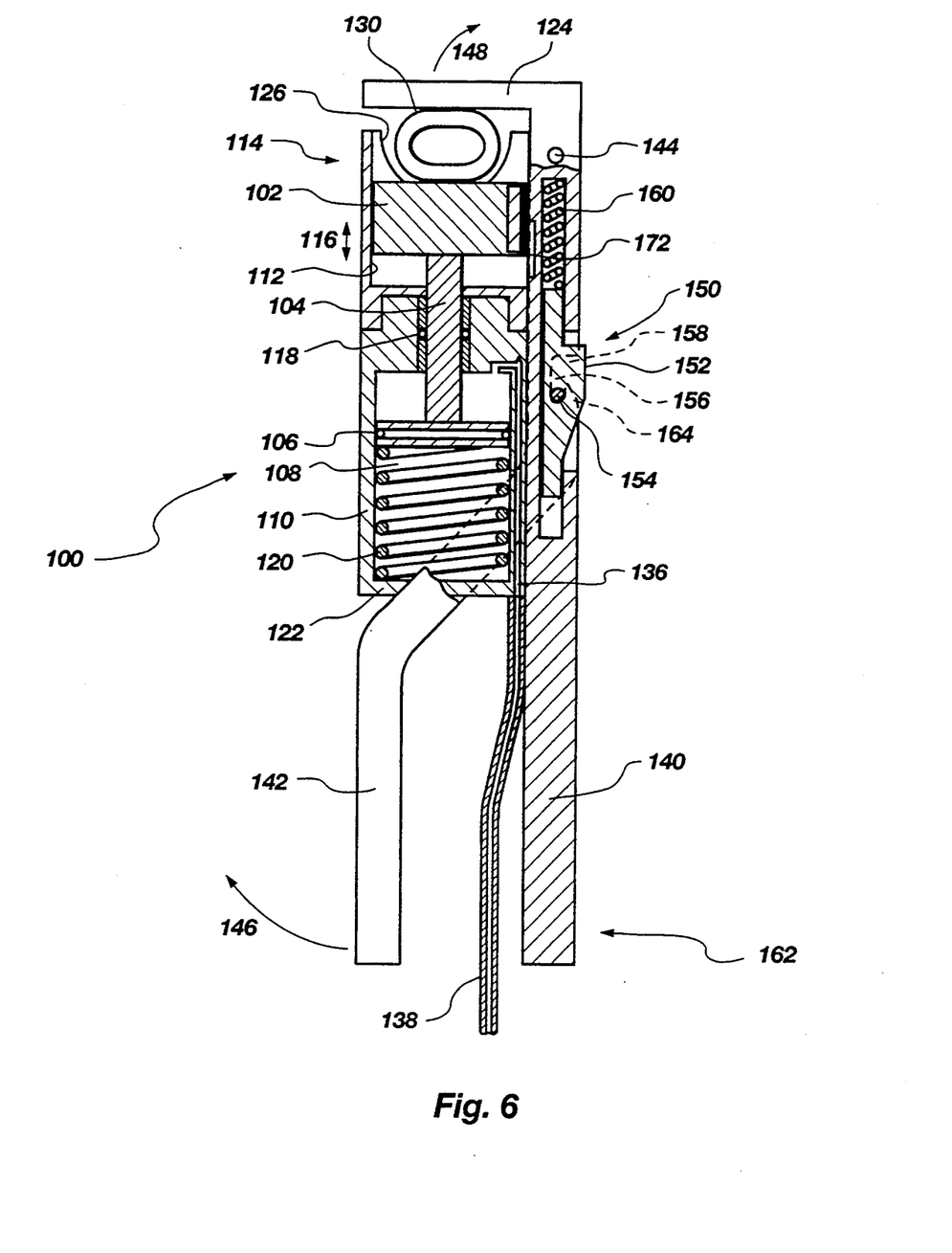
FIG. 6 is a side view is cross-section of the embodiment shown in FIG. 5 illustrating the device in an open position.
Figure 7:
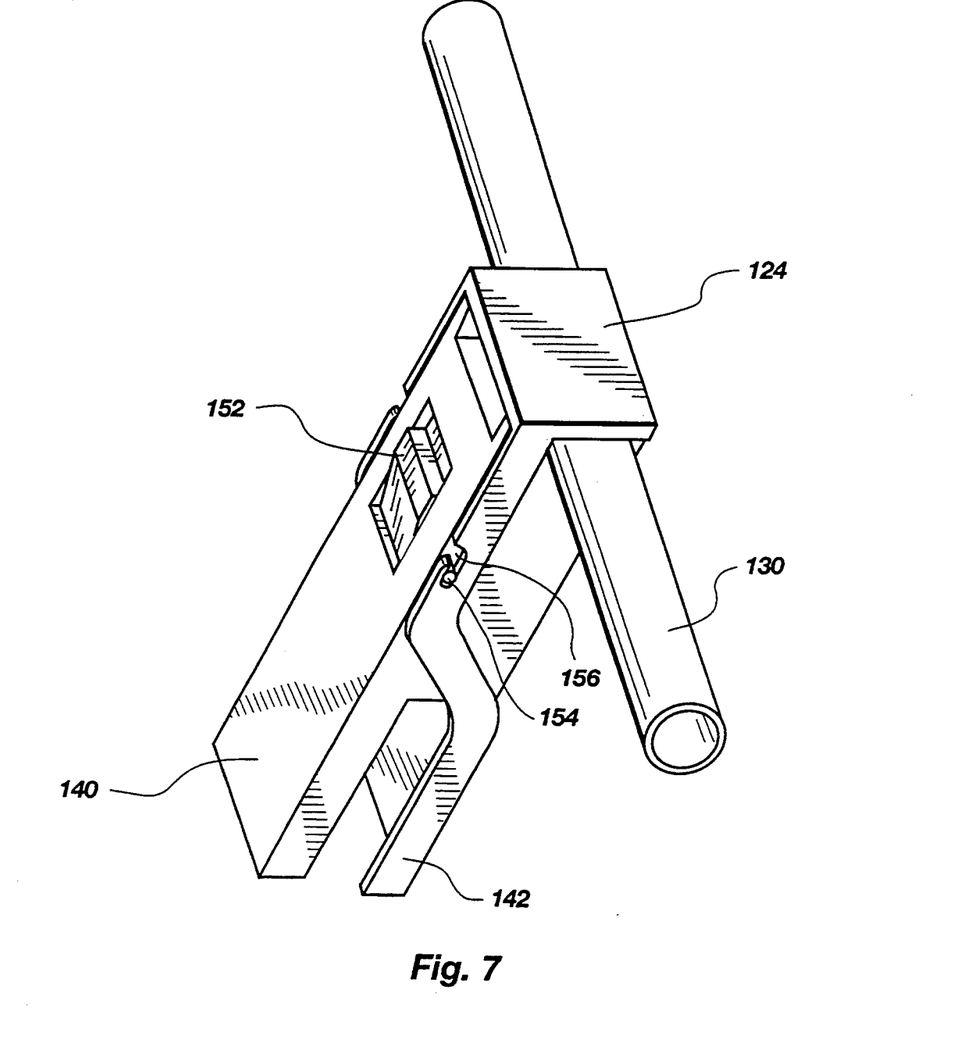
FIG. 7 is a perspective view of the embodiment shown in FIG. 5.

The objectives and purposes for clamping tubes as described above may further be accomplished through employment of an alternative embodiment of the invention shown in FIGS. 5–7. In the alternative embodiment, hydraulic or pneumatic means may be used to provide compression.

As shown in FIG. 5, the clamping structure 100 comprises a clamping bar 102 connected to a movable shaft 104, which is in turn attached to a piston 106 which is slidably positioned within a cylinder bore 108 formed in a clamp housing 110. The clamping bar 102, which may be shaped as a flattened disk, moves up and down within a slot 112 formed in the upper portion 114 of the clamping housing 110. Likewise, movable shaft 104 moves up and down, in the direction shown by arrow 116, through a bearing and seal structure 118.

A spring 120 positioned within the cylinder bore 108 is biased between the bottom 122 of the clamping housing 110 and the piston 106. The spring 120 forces the piston 106 upwardly, which in turn forces the movable shaft 104 through the bearing and seal structure 118, which in turn moves the clamping bar 102 upwardly toward a clamping base 124. A saddle depression 126 (shown in phantom in FIG. 5) is formed in the upper portion 114 of clamping housing 110 and provides a depression within which a tube 130 may reside when the clamping structure 100 is in an open position.

Compressed air may be introduced into the cylinder bore 108 through aperture 134 which receives air from channel 136 formed in the clamping housing 110. Air is fed into channel 136 through a delivery tube 138 which is connected to a source of compressed air (not shown). Introduction of compressed air through aperture 134 causes piston 106 to be forced downwardly thereby compressing spring 120. Thus, it can be seen that the inoperative or initial state of the clamping device 100 is the "closed" position where the tube would be clamped. Only when air is introduced does the piston 106 move causing the movable shaft 104 and clamping bar 102 to move thereby unclamping the tube. FIG. 5 illustrates the clamping structure 100 in the initial or closed state with the tube closed. FIG. 6 illustrates the clamping structure 100 in the open state when air is introduced into the cylinder bore 108, and the tube 130 is open. FIG. 7 also illustrates the clamping structure 100 in the closed state.

The condition detection means previously described are placed in electronic communication with the source of compressed air and act to terminate the supply of compressed air to the clamp when a condition is detected in the system. That is, for example, if the condition detection means is an ultrasound transducer which determines the existence of an air bubble in the tubing, a signal is sent to the compressed air source to cause the compressed air to shut off. With termination of the air, the air within the cylinder bore 108 escapes or is vented off and the piston 106 moves upwardly again causing the clamping bar 102 to pinch off the tube 130. As described previously, when the investigation of the condition or alleviation of the problem permits operation of the system again, compressed air is reintroduced into the system and the tube is opened again.

In addition to the previously described structures, the clamping structure 100 may include a handle 140 forming manual actuation means and a clamping lever 142 which operate to allow placement and compression of the tube 130 between the clamping bar 102 and base 124. The clamping lever 142 pivots about a hinge pin 144 and is rotatable in direction 146 away from the handle 140. The base 124 is connected to the clamping lever 142 and rotates in direction 148 away from the clamping bar 102. A latching mechanism 150 maintains the clamping lever 142 in secure engagement with the handle 140 and prevents movement of the base 124 away from the clamping bar 102.

The latching mechanism 150 comprises a release button 152 which is positioned through a hole formed in the handle 140, as is best illustrated in FIG. 7. Pins 154, positioned on either side of the latching mechanism 150 and connected to the release button 152, are positioned to slidably fit within a slot 156 formed on either lateral side of the clamping lever 142. When the release button 152 is manually pressed upwardly, the pins 154 move upwardly in the direction of clamping base 124 along the slot 156 and are exposed to an opening 158 (shown in phantom in FIG. 5) in the slots 156. The pins 154 are then free to exit from the slots 156 and the clamping lever 142 is free to rotate away from the handle 140.

A spring means 160 normally urges the release button 152 and pins 154 downwardly in the direction of the bottom 112 of the housing 110 to latch the clamping lever 142 into a closed position. To manually close the clamping structure 100, the user grasps the lower portions of the clamping lever 142 and the handle 140, in the general area of 162, and presses the two structures together. The beveled entry 164 to the opening 158 of the slot 156 urges the pin 154 upwardly and into the opening 158. The spring means 160 is concurrently compressed. The pin 154 then enters the slot 156 and decompression of the spring means 160 forces the pin 154 to the end of the slot 156 thereby locking the clamping lever 142 in place.

Partial compression or closure of the tube 130 is desirable under certain conditions, such as weaning the patient from the system as described previously. Partial compression of the tube 130 in this embodiment is accomplished by regulating the amount of compressed air introduced into the cylinder. Regulation of compressed air may be accomplished by, for example, an absolute positioning sensor. An exemplary method is shown in FIGS. 5 and 6 where a permanent magnet 170 is positioned within or relative to the clamping bar 102, and a hall effect sensor and appropriate electronic circuitry contained on a printed circuit board 172 are located on the inside of the clamping structure proximate the clamping bar 102. A suitable hall effect sensor switch may be used is the SS 94A1 made by Microswitch (a division of Honeywell, Freeport, Ill.) As shown in FIG. 5, the handle 140 may serve as a cover to the circuit board and associated circuitry 172. As the magnet 170 moves up and down with the clamping bar 102, the hall effect sensor generates a voltage proportional to the position of the magnet 170. This voltage may be used to control an electric solenoid valve to deliver or vent compressed air from the cylinder bore 108 using common electronic circuitry in a feedback mode (not illustrated).

The present invention is directed to the clamping of tubes or the like, and may be used beneficially in a variety of applications, including, for example, flow monitoring in chemical and biological testing and in fluid systems analysis. The structure of the invention may be modified to meet the demands of the particular application. Hence, reference herein to specific details of the illustrated embodiments is by way of example and not by way of limitation. It will be apparent to those skilled in the art that many additions, deletions and modifications to the illustrated embodiment of the invention may be made without departing from the spirit and scope of the invention as defined by the following claims.

What is claimed:

1. A clamping device for obstructing the flow of fluid through a tube comprising:
   selectively movable clamping means for laterally compressing a tube;
   mechanical compression means associated with said clamping means for providing selective movement to said clamping means;
   power means for providing force to said compression means; and
   condition detection means structured for connection to a tube for detecting a condition therewith, said condition detection means being adapted to provide an actuation signal to said power means upon detection of a condition in the tube.

2. The clamping device according to claim 1 further comprising manual actuation means associated with said compression means for providing manual force to said compression means to compress said tube.

3. The clamping device according to claim 2 wherein said compression means includes a plunger connected to said clamping means, a lever arm interconnected between said plunger and said power means, and a compressible spring mechanism associated with said plunger.

4. The clamping device according to claim 3 wherein said lever arm is adapted to provide movement to said plunger, and the position of said lever arm being adapted to provide stroke distance advantage to said plunger.

5. The clamping device according to claim 4 wherein said clamping means includes a clamping bar and a base, said clamping bar approaching said base when said plunger moves.

6. The clamping device according to claim 4 wherein said power means includes a solenoid.

7. The clamping device according to claim 3 wherein said manual actuation means includes a sleeve associated with said plunger, a handle connected to said sleeve for grasping by a user's hand to impart movement to said sleeve, and a movable cam connected to said sleeve.

8. The clamping device according to claim 1 further comprising indication means positioned proximate to said compression means for indicating a relative degree of compression of said clamping means in compression of said tube.

9. The clamping device according to claim 1 wherein said power means is pneumatic pressure provided by compressed air.

10. The clamping device according to claim 9 wherein said compression means is structured to provide selective movement of said clamping means.

11. The clamping device according to claim 10 wherein said compression means include a spring means biased against said clamping means and positioned to provide force to said clamping means, said spring being compressible by application of said pneumatic pressure.

12. The clamping device according to claim 11 further including an absolute positioning sensor comprising a source indicator connected to said clamping means and an electromagnetic locator means for detecting the location to said source indicator, said electromagnetic locator means being in electrical communication with said compression means to regulate selective actuation of said compression means responsive to movement of said clamping means.

13. The clamping device of claim 1 wherein said mechanical compression means further comprises a plunger connected to said clamping means, said plunger providing movement of said clamping means to effect compression of said tube, and a lever arm connected to said plunger to impart movement to said plunger; and further wherein said power means is connected to said lever arm providing movement to said lever arm, said clamping device further comprising a spring mechanism connected to said plunger to provide movement to said plunger, and means for grasping associated with said plunger for providing manual movement of said plunger to effect compression of said tube.

14. The clamping device according to claim 13 wherein said connection of said lever arm to said power means provides a stroke distance advantage to movement of said plunger.

15. The clamping device according to claim 14 wherein said clamping means further comprises a clamping bar connected to said plunger, a base upon which said tube is positioned, said clamping bar approximating said base when said plunger moves, and further comprising support means for maintaining said tube between said clamping bar and said base.

16. The clamping device according to claim 15 further comprising a sleeve slidably positioned about said plunger, said means for grasping being secured to said sleeve, and further comprising a movable cam secured to said sleeve and biased against a stationary cam.

17. The clamping device according to claim 16 further comprising indication means associated with said movable cam for indicating when said clamping bar has approached said base to fully compress said tube therebetween.

18. The clamping device according to claim 17 wherein said power means is a solenoid.

19. The clamping device according to claim 17 wherein said condition detection means is an air detection device.

20. The clamping device according to claim 17 wherein said condition detection means is a flow direction monitoring device.

21. The clamping device according to claim 17 further comprising alarm means interconnected to said indication means and said condition detection means providing audible indication of incomplete compression of said tube.

22. The clamping device of claim 1 wherein said clamping means comprises:
a clamping bar for compressing a tube;
a plunger connected to said clamping bar, said plunger providing movement of said clamping bar against said tube to effect compression thereof;
a sleeve slidably disposed over said plunger, said sleeve having a slot formed therein for extension of said clamping bar therethrough;
a handle connected to said sleeve for grasping by a person; and
a lever arm connected to said plunger providing movement to said plunger;
and wherein said power means is a solenoid connected to said lever arm providing movement to said lever arm, said clamping device furor comprising a housing sized to enclose said plunger, said lever arm, and said solenoid; a spring mechanism positioned about said plunger and biased between said lever arm and said housing; a stationary cam connected to said housing, said sleeve being rotatably disposed through said stationary cam; a movable cam connected to said sleeve, said movable cam being biased against said stationary cam; and switch means connected to said housing and intermittently contacting said movable cam for indicating when said clamping bar is fully compressing said tube.

23. The clamping device according to claim 22 further comprising air detection means linked to said tube and connected to said solenoid providing a signal to said solenoid when air is detected in said tube.

24. The clamping device of claim 1 further comprising support means for contacting a tube, said support means being oriented in opposing position to said movable clamping means for compressing a tube therebetween.

25. The clamping device of claim 24 wherein said compression means further comprises a spring means biased against said clamping means to provide force thereagainst to maintain said clamping means in a compressed state proximate said support means, said spring means being selectively compressible.

26. The clamping device of claim 25 wherein said movable clamping means includes a clamping bar positioned to contact a tube, a movable shaft member connected to said clamping bar, and a piston connected to said movable shaft member, said spring means being biased against said piston.

27. The clamping device of claim 26 wherein said power means provides force to said piston to provide selective compression of said spring means, said compression of said spring means providing selective movement of said clamping means away from said support means.

28. The clamping device of claim 27 wherein said power means is pneumatic pressure provided by compressed air, said compressed air being selectively supplied to compress said spring means responsive to said signal from said condition detection means.

29. A clamping device for selectively compressing a tube comprising:

a housing structure;

tube positioning means formed in said housing for retaining a tube thereagainst;

movable clamping means positioned relative to said housing structure for selectively compressing said tube;

compression means positioned within said housing structure and connected to said movable clamping means for imparting selective movement to said clamping means;

power means associated with said housing and positioned for providing movement of said compression means; and tube securement means removably attached to said housing and positioned for securing said tube in position relative to said tube positioning means.

30. The clamping device of claim 29 further including selective movement means associated with said clamping means for imparting selective compression to said clamping means.

31. The clamping device of claim 27 wherein said power means is pneumatic pressure provided by compressed air.

* * * * *

UNITED STATES PATENT AND TRADEMARK OFFICE
CERTIFICATE OF CORRECTION

PATENT NO. : 5,445,613

DATED : August 29, 1995

INVENTOR(S) : Jeffrey L. Orth

It is certified that error appears in the above-indentified patent and that said Letters Patent is hereby corrected as shown below:

In Column 8, line 53, change "therewith" to --therewithin--;

In Column 9, line 28, after "means" change "include" to --includes--;

In Column 9, line 36, after "location" change "to" to --of--;

In Column 10, line 37, change "furor" to --further--; and

In Column 12, line 18, change "27" to --30--.

Signed and Sealed this

Fifth Day of December, 1995

Attest:

BRUCE LEHMAN

Attesting Officer

Commissioner of Patents and Trademarks